United States Patent
Boveja et al.

(10) Patent No.: US 7,588,567 B2
(45) Date of Patent: *Sep. 15, 2009

(54) METHOD AND SYSTEM OF STOPPING ENERGY DELIVERY OF AN ABLATION PROCEDURE WITH A COMPUTER BASED DEVICE FOR INCREASING SAFETY OF ABLATION PROCEDURES

(75) Inventors: Birinder R. Boveja, Milwaukee, WI (US); Angely Widhany, Milwaukee, WI (US)

(73) Assignee: ABL Technologies, LLC, Milwaukee, WI (US)

( * ) Notice: Subject to any disclaimer, the term of this patent is extended or adjusted under 35 U.S.C. 154(b) by 74 days.

This patent is subject to a terminal disclaimer.

(21) Appl. No.: 11/146,601

(22) Filed: Jun. 7, 2005

(65) Prior Publication Data

US 2005/0251130 A1    Nov. 10, 2005

Related U.S. Application Data (63) Continuation of application No. 11/112,648, filed on Apr. 22, 2005.

(51) Int. Cl.
*A61B 18/16* (2006.01)
(52) U.S. Cl. .......................... 606/34; 128/898; 606/38
(58) Field of Classification Search ............. 606/32–34, 606/37–42, 45–50; 607/100–102, 115, 116, 607/154–156, 96; 128/898
See application file for complete search history.

(56) References Cited

U.S. PATENT DOCUMENTS

| | | | | |
|---|---|---|---|---|
| 5,507,743 A | * | 4/1996 | Edwards et al. | 606/41 |
| 5,837,001 A | | 11/1998 | Mackey | 607/102 |
| 6,233,490 B1 | * | 5/2001 | Kasevich | 607/101 |
| 6,663,622 B1 | * | 12/2003 | Foley et al. | 606/34 |
| 6,679,269 B2 | * | 1/2004 | Swanson | 128/898 |
| 6,730,078 B2 | | 5/2004 | Simpson et al. | 606/34 |
| 6,923,804 B2 | * | 8/2005 | Eggers et al. | 606/34 |
| 7,192,427 B2 | * | 3/2007 | Chapelon et al. | 606/33 |
| 2004/0059237 A1 | | 3/2004 | Narayan et al. | 600/509 |
| 2004/0078036 A1 | | 4/2004 | Keldar | 606/41 |
| 2004/0127894 A1 | | 7/2004 | Eick et al. | 606/34 |
| 2005/0148892 A1 | | 7/2005 | Desai | 600/510 |

OTHER PUBLICATIONS

Kottkamp et. al, An anatomically and electrogram-guided stepwise approach for effective and safe catheter ablation of the fast pathway for elimination of atrioventricular node reentry tachycardia, JJAC vol. 25 No. 5 Apr. 1995 p. 974-983.

* cited by examiner

*Primary Examiner*—Henry M Johnson, III
*Assistant Examiner*—Aaron Roane (57) ABSTRACT

An apparatus and method for stopping of ablation energy delivery to tissues during cardiac ablation procedures provides added safety. The apparatus uses control switch mechanism comprising relay switch and circuitry inserted between the ground patch and ablation generator. Alternatively, the control switching means can be on the catheter side of the ablation circuit. The switching mechanism is connected to a computer, which controls the on-off switch based on predetermined conditions. When the control switch part of the circuit is opened, the ablation generator shuts of immediately. The software in the computer is configured, such that the computer controlled stopping of energy delivery only occurs when patient safety is at risk.

13 Claims, 8 Drawing Sheets

METHOD AND SYSTEM OF STOPPING ENERGY DELIVERY OF AN ABLATION PROCEDURE WITH A COMPUTER BASED DEVICE FOR INCREASING SAFETY OF ABLATION PROCEDURES

This application is a continuation of application Ser. No. 11/112,648 filed Apr. 22, 2005, entitled "Method and system of increasing safety of cardiac ablation procedures" and is related to a co-pending application entitled "Method and system for monitoring atrial fibrillation ablation with an ablation interface device". These applications are incorporated herein in their entirety by reference.

FIELD OF INVENTION

The present invention relates to catheter ablation, more specifically method and apparatus for increasing the safety of transcatheter ablations by computer based stopping of energy delivery.

BACKGROUND

Many cardiac arrhythmia's that formerly required the use of potentially toxic drugs or cardiac surgery can now be routinely cured (or at least palliated) in the electrophysiology laboratory by means of transcatheter ablation techniques. Atrial and ventricular tachyarrthmia's are routinely ablated using catheter ablation techniques. Some of the commonly ablated arrythmia's are AV nodal reentry tachycardia (AVNRT), accessory pathway mediated tachycardia (AVRT), atrial flutter, atrial fibrillation, normal heart ventricular tachycardias (VT), and ischemic heart VT. Ablations for atrial fibrillation (using pulmonary vein isolation or substrate modification techniques) are procedures that are becoming increasing common, since atrial fibrillation is a significant health issue.

Complications of catheter based ablation procedures include AV heart block, perforations of the heart muscle particularly of thin structures like the atria, and risk of emboli particularly when ablating on the left side of the heart, such as left atrium or left ventricle.

During certain ablation procedures, a backup system where a software based instrument is capable of stopping ablation energy delivery, is highly desirable and may prevent serious complications such as complete heart block, and subsequent pacemaker implant, among other complications. Such a system can also be used in non-cardiac ablations of other organs such as stomach and liver.

Applicant's related co-pending application Ser. No. 11/112,648 (filing date Apr. 22, 2005) entitled "Method and system of increasing safety of cardiac ablation procedures", and co-pending application entitled "Ablation interface device for monitoring catheter ablations for atrial fibrillation" are generally directed to a novel PC based system that interfaces with both the patient and the ablation generator for providing added safety to the ablation procedures. These patent applications are incorporated herein in their entirety by reference. Such system finds uses in different types of cardiac ablation procedures, particularly left atrial ablations for atrial fibrillation, and slow pathway modification for providing ablation therapy of AV nodel reentry tachycardia (AVNRT).

For procedures such as AVNRT, and left atrial (or ventricular) ablations among other procedures, there are many situations where a quick and prompt cessation of ablation energy delivery can prevent a major complication. This patent application is directed to novel method and system for stopping energy delivery of an ablation procedure utilizing a computer initiated switching-control means. Pre-determined criteria's are set based on one or more parameters, for the computer program to detect the occurrence of a pre-determined event and send a command to stop ablation energy delivery. This provides an extra level of safety to the procedure.

PRIOR ART

Prior art search reveals U.S. patent application Ser. No. 10/407,905 (Eick et al.), which is generally directed to ablation catheter operation feedback, thereby providing the clinicians with increased options for programmable control of the ablation catheter.

The Eick '905 patent application mainly discloses use of LocaLisa mapping system for monitoring the location and movement of the ablation catheter. The applicant's invention is directed to monitoring the patient's electrograms and the relationship between electrograms using an ablation interface system, which is a totally different concept.

U.S. patent application Ser. No. 10/277,079 (Keidar) is generally directed to real-time monitoring and mapping of ablation lesion formation in the heart. The means, functionality, and intent of the Keidar '079 application is significantly different than applicant's disclosure. In the Keidar '079 disclosure a conventional mapping system is used with an endocardial mapping and ablation catheter, to monitor energy delivery to individual lesions and represent the lesion pictorially on a computer generated map. Among other things, the intent is "if user 22 determines that a particular site or region has not been sufficiently ablated, he can immediately return to the site and repeat the ablation procedure" paragraph [0133], lines 20-22, on page 8.

In contrast, in applicant's system and method, the patient is monitored, as well as, the whole ablation procedure is monitored as opposed to individual lesions, using an ablation interface system, where both electrical parameters and physiological parameters are measured, processed, and displayed. Further, in applicant's disclosure if predetermined conditions are reached, a software guided instrument based interruption of energy delivery occurs which acts as safety alarm, and which may be simply reset to continue on with the procedure.

SUMMARY OF THE INVENTION

Currently in ablation procedures, a physician operator decides when to turn-off ablation energy during a procedure, and conveys that instruction to an assistant operating an ablation generator. Many times the ablation procedures result in complications due to excessive ablation energy delivery. The apparatus and method of this disclosure is intended to reduce complications and increase safety for the patients undergoing ablation procedures.

Accordingly, in one object of the invention a computer controlled system automatically turns-off ablation energy, if patient's safety is at risk.

Another object of the invention is to increase safety of cardiac ablation procedures.

Another object of the invention is to increase safety of ablation procedures on the stomach and liver.

In another aspect of the invention, a control switch is inserted on the ground loop side of the ablation circuit.

In another aspect of the invention, the control switch comprises a relay switch and circuitry connected to a computer.

In another aspect of the invention, a computer triggers the control switch based on software.

In another aspect of the invention, the computer software utilized is one from a group comprising, Lab Windows/CVI, LabView (National Instruments Corp.), Microsoft Visual C++, Dot Net framework, MATLAB, Microsoft Visual Basic.

In another aspect of the invention, the computer may be part of an electrophysiology recording system.

In yet another aspect of the invention, the computer may be part of a mapping system.

Various other features, objects and advantages of the invention will be made apparent from the following description taken together with the drawings.

BRIEF DESCRIPTION OF THE DRAWINGS

For the purpose of illustrating the invention, there are shown in accompanying drawing forms which are presently preferred, it being understood that the invention is not intended to be limited to the precise arrangement and instrumentalities shown.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
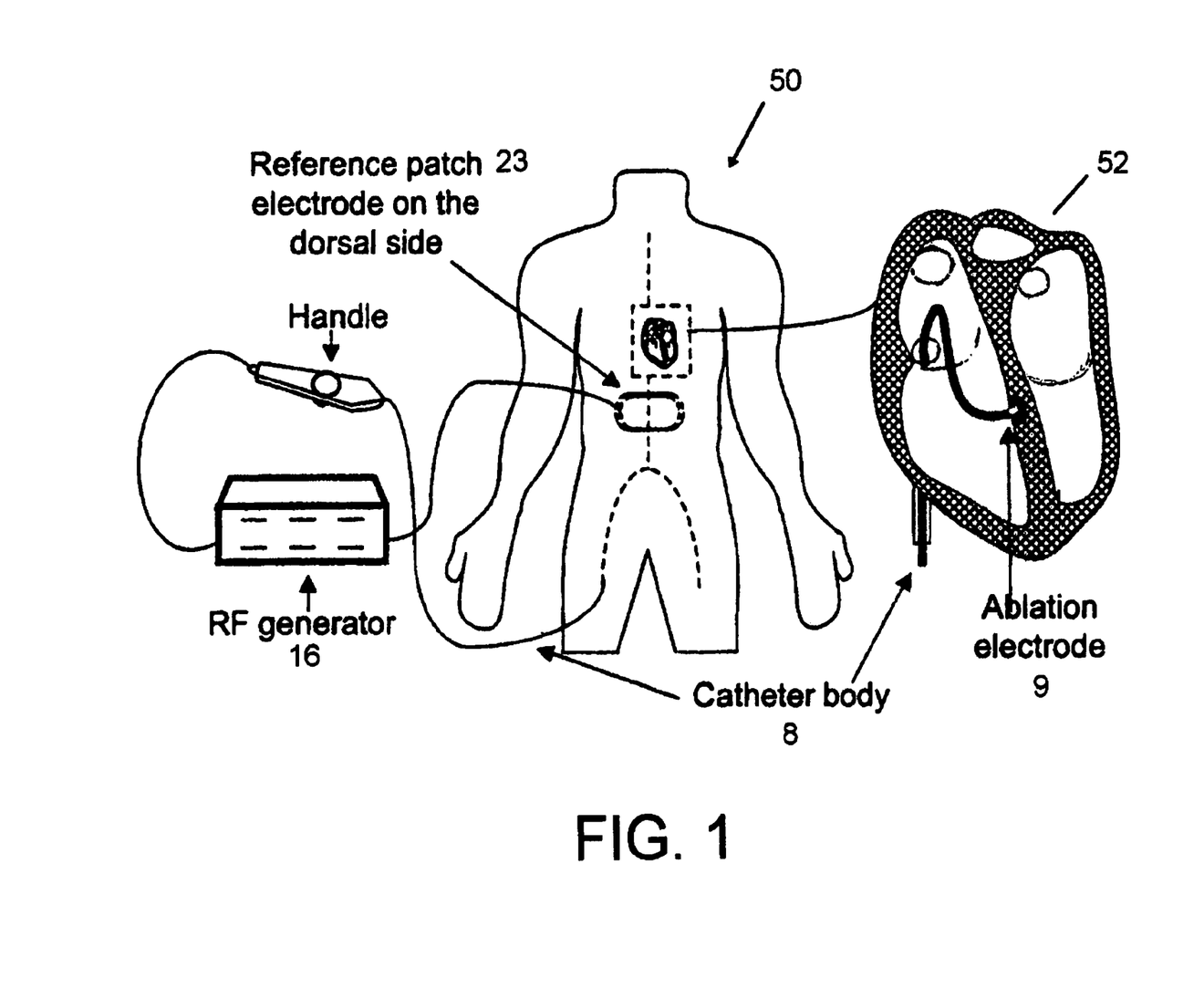
FIG. 1 depicts general concept for cardiac ablation procedures.

As shown in conjunction with FIG. 1, the basic idea behind transcatheter ablation is to position an electrode catheter to a critical area within the heart 52, and to apply damaging energy through the catheter in order to create a discrete scar. Strategically placed scar tissue, since it is electrically inert, can disrupt the pathways necessary for pathologic tachyarrhythmias.

Figure 2:
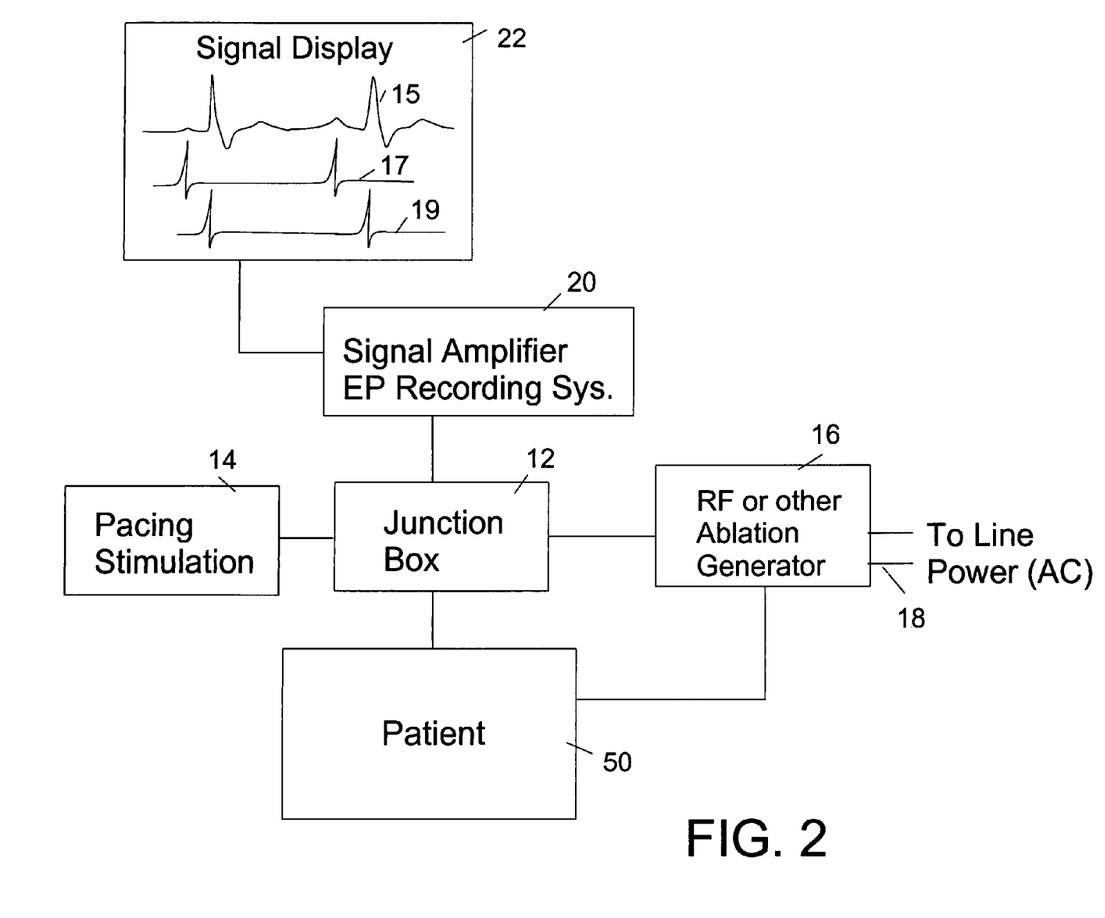
FIG. 2 depicts a general setup of cardiac ablation procedures.

For the purposes of explaining the methodology of the current invention, it is instructive to understand a typical setup for a generic cardiac ablation procedure. Shown in conjunction with FIG. 2 is a typical setup, where body surface ECG 15 (usually 12 lead), atrial intra-cardiac (IC) signal 17, ventricular intra-cardiac (IC) signal 19, and other intra-cardiac (IC) signals such as His bundle recording (not shown) and coronary sinus signals (not shown) are obtained from the patient 50, via transvenous diagnostic catheters. The catheters in the body are connected via extension cables to a junction box 12. The body surface signals are typically amplified by amplifiers of an EP recording system 20 and displayed on a display monitor 22 for easy visualization during the Electrophysiology (EP) study and cardiac ablation procedure. A pacing stimulator 14 is also connected (typically via junction box 12) for pacing of different sites within the heart such as the atrium or ventricle for example. An ablation generator 16 is connected to the patient 50. If a radiofrequency (RF) generator is used, a ground patch 23 or reference patch 23 which is typically connected on patient's back (FIG. 1) is connected to the RF ablation generator, and an ablation catheter 37 positioned inside the heart 52 and connected to the RF ablation generator 16 via connector cables completes the circuit for ablation procedure to proceed.

Typically a physician manipulates and positions the ablation catheter while being next to the patient's table, and another person operates the ablation generator 16. The physician positioning the ablation catheter is also able to operate the ablation generator via a foot paddle, even though that is typically not done.

In the method and system of this disclosure, a software controlled instrument system can automatically stop the energy delivery of ablation generator, when certain pre-determined criteria's/threshold are reached. This is used as a backup system to increase the safety of cardiac ablation procedure for various arrhythmia's. Even though the system and method is described in conjunction with examples of AVNRT and atrial fibrillation ablation, this system and method may be used in any cardiac ablation procedures.

Examples for Use with AVNRT Ablations

In ablation procedures such as for A-V nodel re-entry tachycardia (AVNRT) or antero-septal accessory pathway ablation, it is imperative to stop the ablation generator energy after the first A-V disassociated beat. In the current clinical practice it can frequently take two to five seconds (sometimes even more) to stop the ablator energy, since the physician has to recognize the dropped (A-V) beat, communicate it to the person operating the ablation generator, and the reaction time of the person operating the ablation generator 16. The 2 to 5 seconds that it frequently takes, puts the patient at risk for complete heart block (A-V block), which may necessitate implantation of a cardiac pacemaker for maintaining patient's cardiac rhythm.

As detailed in a co-pending application (Ser. No. 11/112, 648), it is highly desirable to have a method and system where after sensing one atrial-ventricular blocked beat, the power of the ablation generator is interrupted immediately without the delay of the human reaction time. It is known from clinical experience, that where ablation power is interrupted after the first (A-V) dropped beat, the likelihood for the patient developing complete heart block is not very significant, thereby avoiding cardiac pacemaker implantation.

In the method and system of this disclosure, a computer based interface device performs analysis of the relationship between atrial and ventricular signals, and after sensing one disassociated beat between atrial and ventricular signals, the device automatically activates a switch which disconnects or removes power from the ablation generator whereby disrupting ablation generator energy. This allows for the physician to reposition ablation catheter to a slightly different position within the heart, reset the device and ablation generator 16, and start delivering ablation energy again. This procedure can be repeated as many times as necessary until the desired end point of the ablation is reached.

Figure 3:
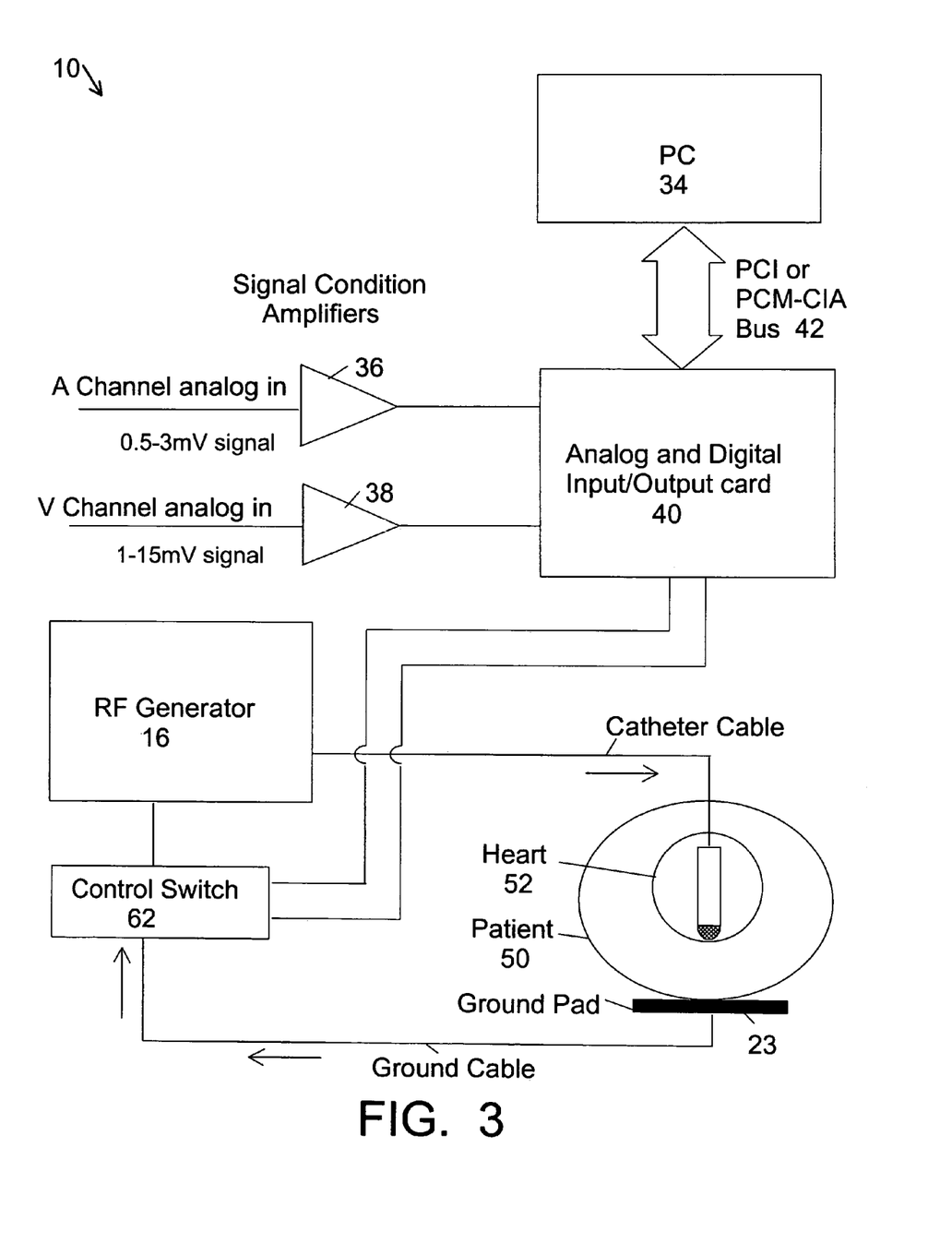
FIG. 3 is a simplified block diagram showing a control switch 62 on the ground side of an ablation circuit which is controlled by a computer.

Shown in conjunction with FIG. 3 is a simplified block diagram of one aspect of the current invention, which is referred to as Ablation Interface Device (AID) 10. As was shown in FIG. 3, atrial signal from high right atrium (HRA)

and ventricular signal from right ventricle (RV) are brought in the Ablation Interface Device (AID) 10 by splitting the signal from the junction box 12. Atrial signals which are typically in the 0.5 mV to 3 mV range, and ventricular signals which are typically in the 1-15 mV range, are isolated from the patient 50 using standard techniques known in the art. Signal conditioning such as amplification and filtering is also performed using standard amplification and filtering techniques. From signal conditioning amplifier 36, 38 the signal is connected to a data acquisition system 40 for bringing the two channel information for processing and analyzing the signals. The DAQ system may be a plug-in board for a desktop PC, a plug-in PCM-CIA card for a laptop, or an external DAQ unit connected to the PC or laptop via a fast USB port. All of these data acquisition systems are available from National Instruments Corp. (Austin, Tex.), and other manufacturers.

The conditioned signals, i.e. the high right atrial (HRA) and ventricular (V) recording, are analyzed real time using the processor and software in the laptop PC or desktop PC. The software analyzes the information from the intra-cardiac recording real-time. When the pre-determined criteria are met, i.e. where the safety of ablation is in question, the computer will automatically stop the delivery of ablation energy to the patient. Advantageously, computer controlled operations will be much quicker, and in many cases will prevent the patient from getting heart blocked, and pacemaker implanted.

The computer may turn off the power supply of the RF via a relay switch. Shown in conjunction with FIG. 3, the control switch 62 is adapted to be placed between the ground cable 23 and the RF generator 16. RF generators typically monitor the impedance of the circuit. If the impedance increases above a specified level, or if the generator detects an open circuit, the RF generator will shut off immediately, and the ablation generator will display an error message.

It will be clear to one of ordinary skill in the art that the computer 34 may be a dedicated computer, or the computer may be a part of an electrophysiology mapping system, such as the Pruca monitoring system available from GE Medical Systems (Milwaukee, Wis.). Alternatively the computer 34, may be part of a mapping system. The mapping system may be any of the commercially available cardiac mapping system. Examples of four cardiac mapping systems are:

a) Carto mapping system, which is an electroanatomical mapping system available from Biosense/Webster (Diamond Barr, Calif.);

b) Navix or Ensite mapping systems available from Endocardial Solutions, a division of St. Jude Medical (MN);

c) RPM mapping system available from Boston Scientific; and d) Local Lisa mapping system available from Medtronic Inc. (Minneapolis, Minn.).

Example for Atrial Fibrillation Application

Figure 4A:
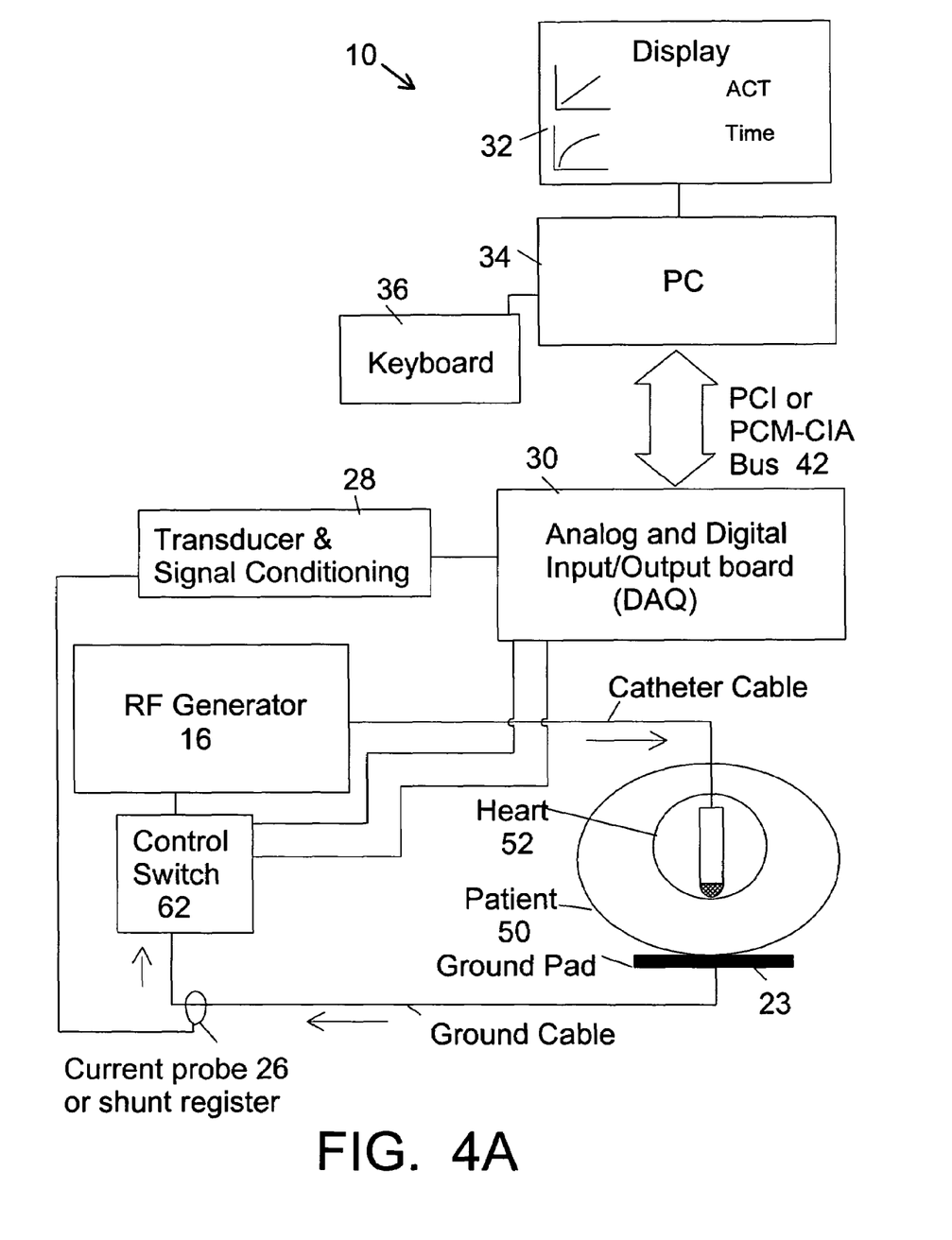
FIG. 4A is a simplified block diagram where computer controlled stopping of ablation can occur via a control switch in the ground loop, for atrial fibrillation procedures.

Shown in conjunction with FIG. 4A is a simplified block diagram of the method and system as applied to atrial fibrillation ablation procedure performed in the left atrium. Since the ablation lesions are performed in the left side of the heart (in arterial blood), physicians are careful to limit the cumulative energy delivered because of the potential for emboli formation.

Figure 4B:
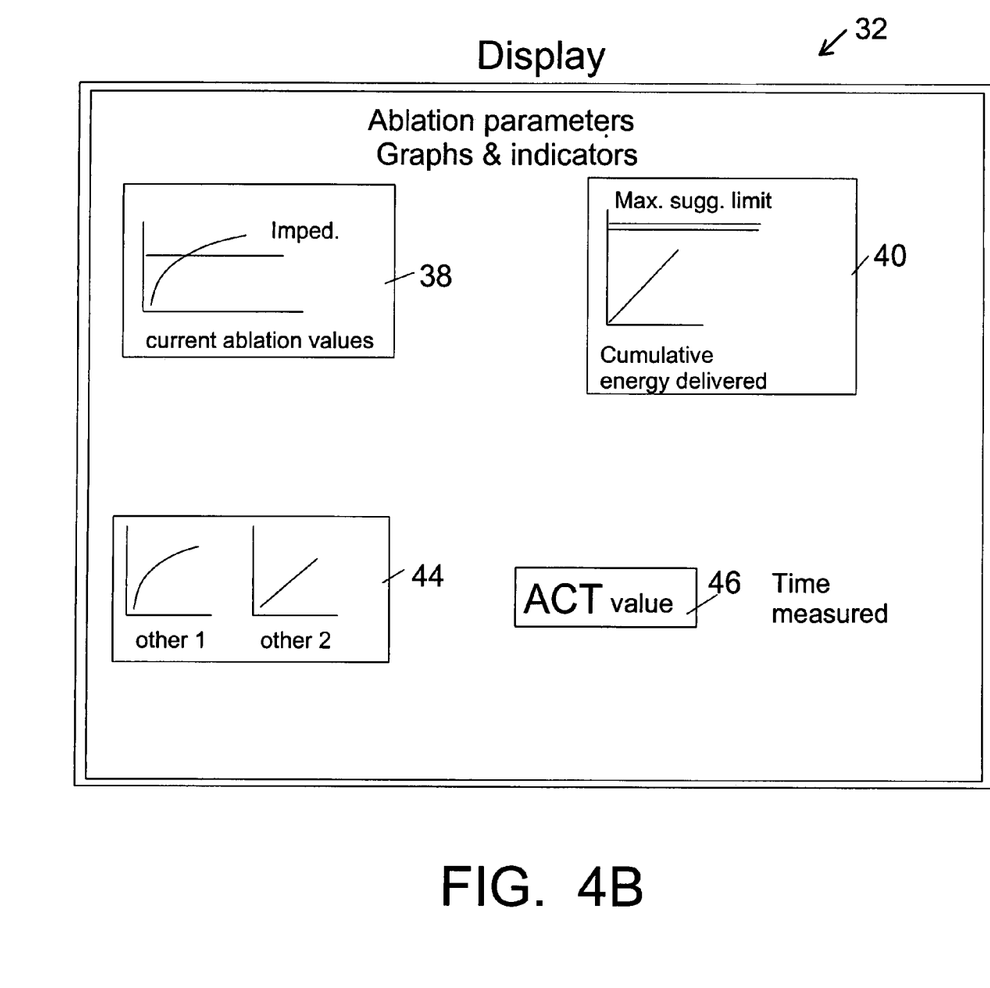
FIG. 4B shows an example of display for atrial fibrillation procedures.

As shown in FIG. 4A, a current probe 26 or other means are used to obtain information from the ablation circuit. The electrical signal information is conditioned and fed into a computer 34 via Analog and Digital I/O board (DAQ) 30. The software is configured to calculate the total energy delivered and display the information on a graph. As shown in conjunction with FIG. 4B of the display, when a pre-determined level is reached (shown in frame 40), the software sends a signal to the output side of the interface board. A control switching means is activated and energy delivery from the ablation generator 16 is stopped. A reset button is pressed to continue with the ablation procedure.

It will be clear to one skilled in the art, that in addition to the AVNRT and atrial fibrillation examples given above, there are many other situations where instrument (computer) control of stopping energy delivery can prevent serious complications. It will also be understood, that such apparatus and method can also be used in non-cardiac ablations of other organs such as stomach and liver.

Figure 5:
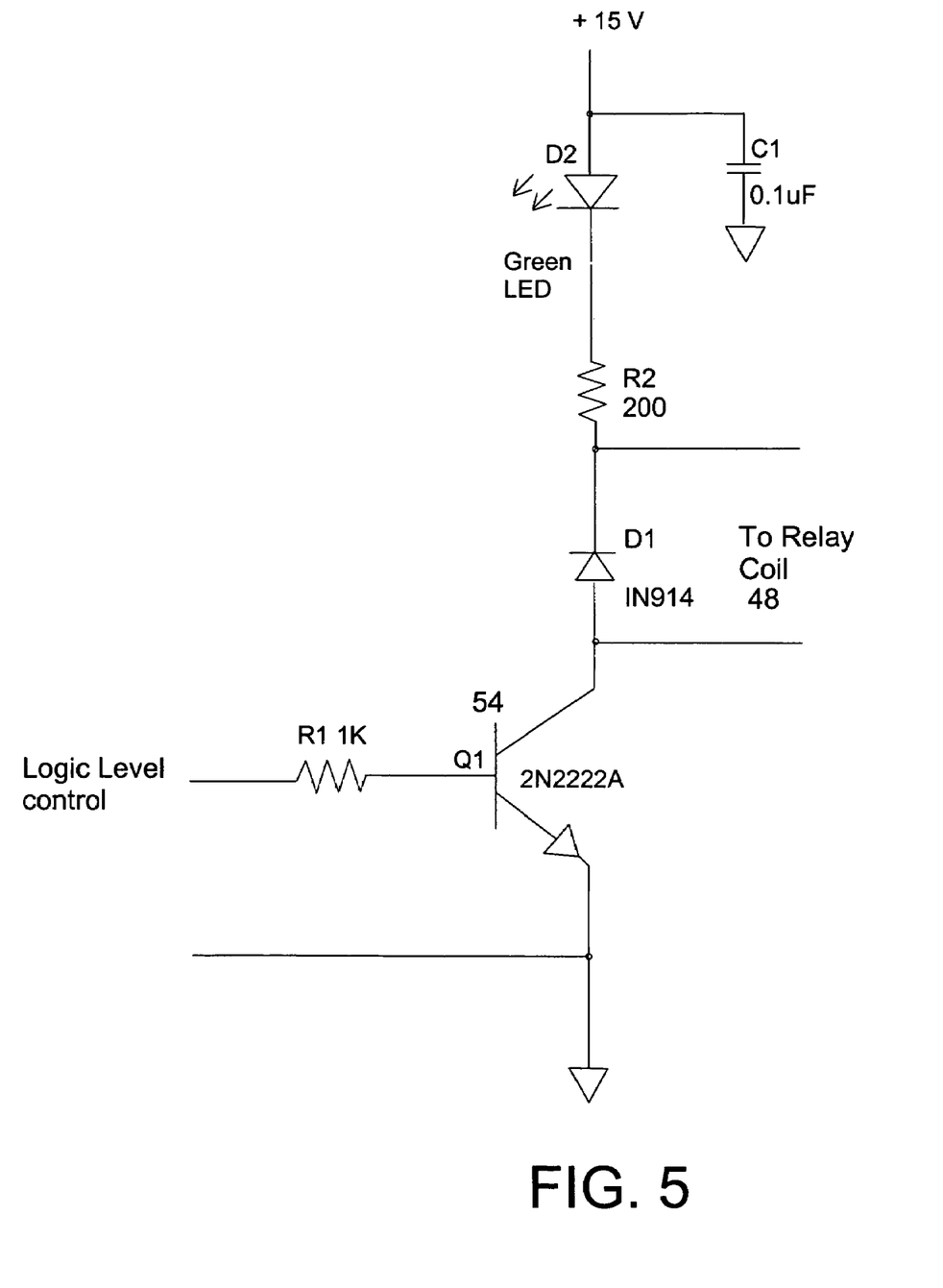
FIG. 5 depicts a relay driver circuitry of the invention.
Figure 6:
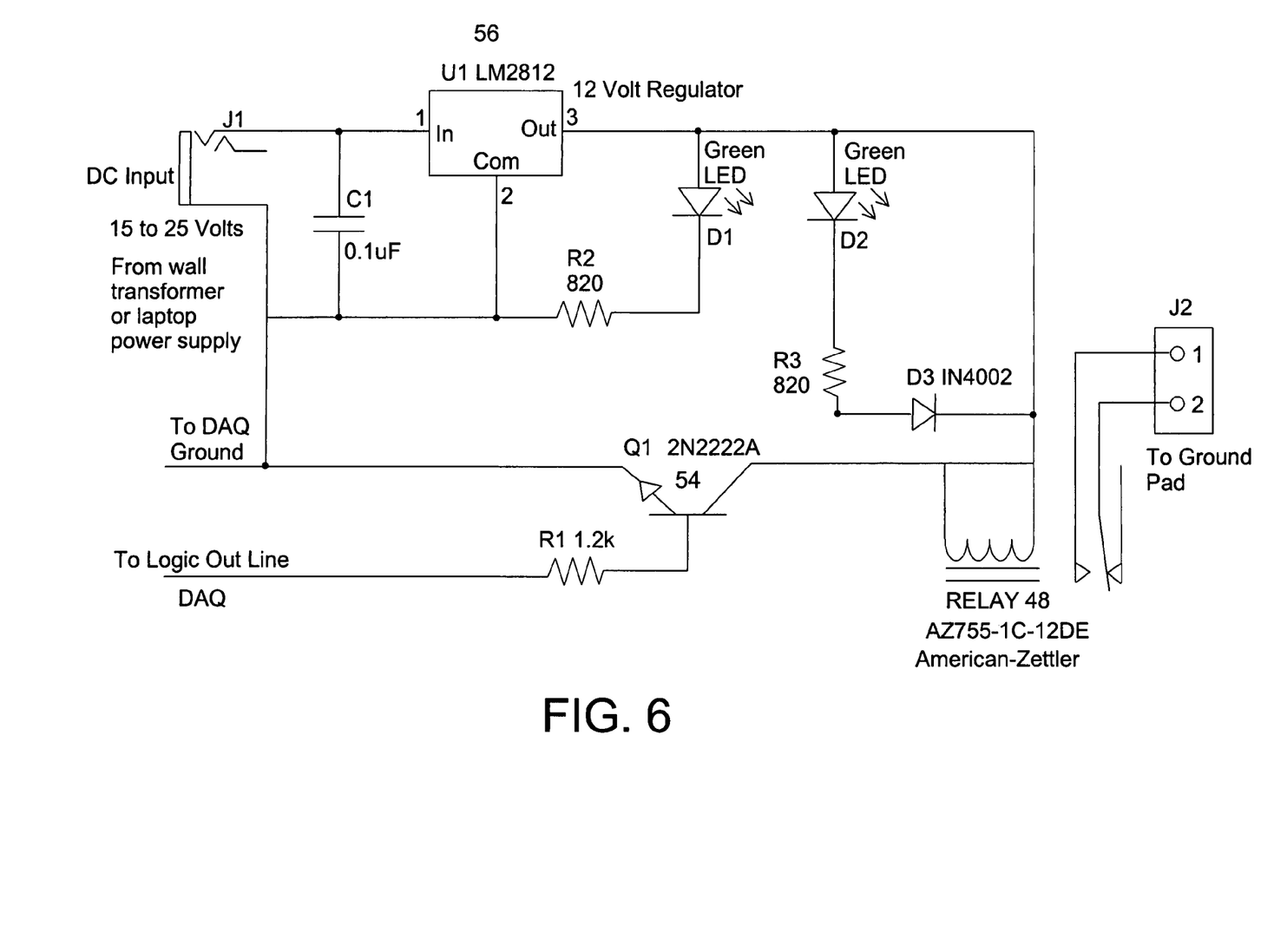
FIG. 6 depicts one implementation of ground circuit interruption to automatically stop ablation generator energy delivery.

The implementation of the concept is shown in conjunction with FIGS. 5 and 6. FIG. 5 shows a simplified circuit to drive a relay coil 48, which interrupts the ground loop side of the ablation circuit. As shown in the figure, when the logic level control 54 goes high, there is current flow at the base of transistor Q1 (54), and transistor Q1 conducts, energizing the Relay coil 48. Shown in conjunction with FIG. 3 (and FIG. 4A), the logic level control 54 is high only when certain pre-determined conditions are met. The pre-determined conditions are derived by analysis of signals and are typically based on safety conditions.

Most ablation generators on the market have maximum impedance cut-off and delta impedance cut-off features. In this feature, when the impedance increases over the adjusted maximum cut-off value or is infinite (e.g. if the connection to the catheter is broken) the ablation generator will switch off automatically and an error message "Imp. too high" will be displayed.

Using this feature of the ablation generator, shown in FIG. 6 is one implementation for practicing this method. In this embodiment, Logic High energizes the relay, thereby shutting off the ablation generator.

As shown in conjunction with FIG. 6, a relay switch circuitry is connected in the ground patch electrode 23. In this configuration, a transistor Q1 54 performs the switching. When the Logic Out Line from the DAQ goes "high", the relay is energized. Power to the circuit may be supplied from a wall transformer or laptop power supply. The logic out line from DAQ is controlled by the software. The software is configured such that for AVNRT, the control is based on timing relationships between atrial and ventricular signals. For atrial fibrillation application, the control may be based on the cumulative energy reaching a pre-determined level.

Among the software that can be used is LAB VIEW® (National Instruments Corp.), LAB WINDOW/CVI®, MICROSOFT VISUAL C++®, DOT NET FRAMEWORK®, MATLAB®, MICROSOFT VISUAL BASIC®. Additional suitable software may also be used.

In one preferred embodiment, the circuitry shown in FIG. 6 is encased in a small enclosure and physically connected to a commercially available ground patch. One such ground patch is disclosed in U.S. Pat. Nos. 5,611,709, 4,750,482, and 4,699,146, and available from Valleylab (a division of Tyco Healthcare, Boulder, Colo.). These patents are incorporated herein by reference. In this embodiment, the wires of the ground patch are cut and the circuitry of FIG. 6 is inserted into the ground patch. As shown in the figure, the base of the transistor Q1 is connected to a Logic Out line of the DAQ interface, and the emitter of Q1 is connected to the ground of DAQ interface board.

Figure 4C:
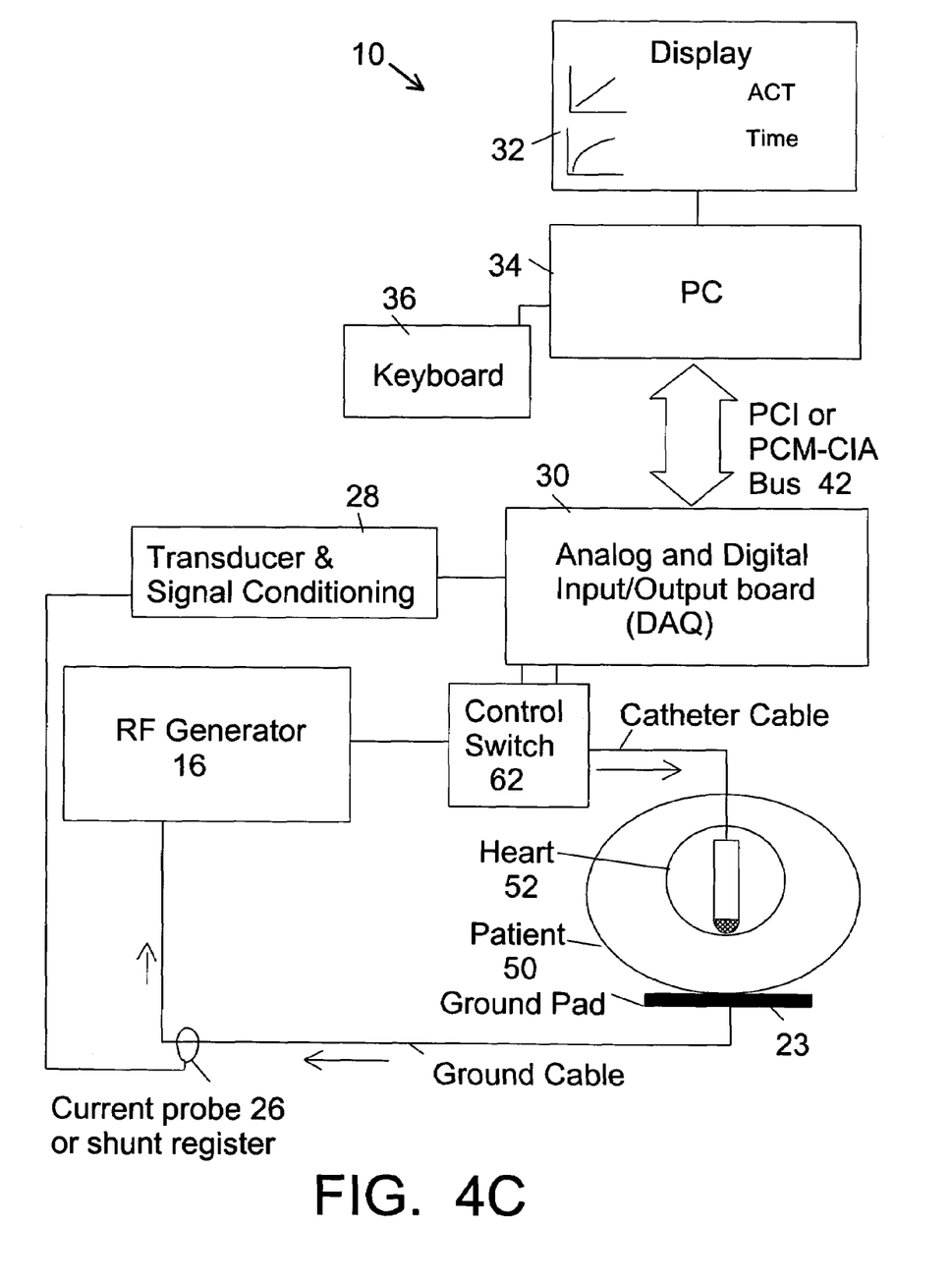
FIG. 4C is a simplified block diagram where computer controlled stopping of ablation can occur via a control switch on the catheter side of the ablation circuit.

It will be understood from the above disclosure that even though in the preferred embodiment, the control switching mechanism is inserted in the ground loop of the ablation circuit, with only slight modifications the same circuitry can also be inserted on the catheter side of the ablation circuit, i.e. between the ablation generator and the ablation catheter (as is shown in FIG. 4C).

The present invention may be embodied in other specific forms without departing from the spirit or essential attributes thereof. It is therefore desired that the present embodiment be considered in all aspects as illustrative and not restrictive, reference being made to the appended claims rather than to the foregoing description to indicate the scope of the invention.

We claim:

1. A method of shutting-off energy delivery of an ablation procedure, comprising the steps of:
    providing cardiac electrical timing information for shutting-off energy supply to an ablation system, wherein said cardiac electrical timing information is based on timing relationship between atrial and ventricular signals,
    utilizing analysis by a software adapted and configured for detecting an event indicative of an adverse condition based on said cardiac electrical timing information, and
    automatically shutting-off of energy supply to an ablation system utilizing a switching device based on said cardiac electrical timing information which is based on timing relationship between atrial and ventricular signals.

2. The method of claim 1, wherein said switching device comprises a relay switch and a relay switch circuitry and is in a ground loop of said ablation system.

3. The method of claim 1, wherein said switching device comprises a relay switch and a relay switch circuitry and is on a catheter side of said ablation system.

4. The method of claim 1, wherein said analysis by a software utilizes a computer which is part of an electrophysiology monitoring system.

5. The method of claim 1, wherein said analysis by a software utilizes a stand alone computer which is not part of an electrophysiology monitoring or electrophysiology mapping system.

6. The method of claim 1, wherein said software is at least one of being a part of an electrophysiology (EP) monitoring system, or an electrophysiology mapping system, or a computer system other than an electrophysiology (EP) monitoring system or an electrophysiology mapping system.

7. The method of claim 1, wherein said software analyzes information from the intra-cardiac recording real-time.

8. A method of shutting-off the energy delivery by an ablation system comprising the steps of:
    providing cardiac electrical timing information during an ablation procedure,
    detecting at least one of a disassociation of an atrial beat and a corresponding ventricular beat, or changes in timing between atrial and its corresponding ventricular beat from said cardiac electrical timing information, and
    automatically shutting off said ablation system utilizing a relay switching triggered by said disassociation of an atrial beat and a ventricular beat or changes in timing between atrial and its corresponding ventricular beat.

9. The method of claim 8, wherein said ablation procedure is a cardiac ablation procedure for AV Nodal Reentrant Tacycardia (AVNRT).

10. A method of shutting off the energy delivery by an ablation system comprising the steps of:
    providing cardiac electrical timing information, and
    automatically shutting off said ablation system based upon detection of an cardiac event based upon said cardiac electrical timing information, wherein said cardiac event is at least one of a) timing relationship between atrial and ventricular signals, or b) disassociation of an atrial beat and a ventricular beat, or c) changes in timing between atrial and its corresponding ventricular signal.

11. The method of claim 10, wherein said cardiac electrical timing information is from the intra-cardiac recording real-time.

12. The method of claim 10, wherein said cardiac electrical timing information is analyzes by a software within a computer adapted and configured for detecting an event indicative of an adverse condition based on said cardiac electrical signals timing information.

13. The method of claim 10, wherein said shutting off of said energy delivered by an ablation system is by utilizing a switching device further comprising a relay switch and a relay switch circuitry.

* * * * *